United States Patent [19]

Dubief et al.

[11] Patent Number: 6,086,862
[45] Date of Patent: Jul. 11, 2000

[54] COMPOSITION FOR THE TREATMENT OF KERATINOUS MATERIAL, COMPRISING AT LEAST ONE GRAFTED SILICONE POLYMER CONTAINING A POLYSILOXANE SKELETON GRAFTED WITH NON-SILICONE ORGANIC MONOMERS AND AT LEAST ONE ANIONIC POLYMER

[75] Inventors: Claude Dubief, Le Chesnay; Christine Dupuis; Daniéle Cauwet-Martin, both of Paris, all of France

[73] Assignee: L'Oreal, Paris, France

[21] Appl. No.: 08/849,185

[22] PCT Filed: Sep. 6, 1996

[86] PCT No.: PCT/FR96/01432

§ 371 Date: Jun. 26, 1997

§ 102(e) Date: Jun. 26, 1997

[87] PCT Pub. No.: WO97/12592

PCT Pub. Date: Apr. 10, 1997

[30] Foreign Application Priority Data

Sep. 29, 1995 [FR] France .................... 95 11478

[51] Int. Cl.$^7$ .............. A61K 7/075; A61K 7/48
[52] U.S. Cl. ............ 424/70.12; 424/47; 424/61; 424/70.1; 424/70.16; 424/70.17; 424/70.22; 424/401
[58] Field of Search ............ 424/401, 61, 70.1, 424/70.12, 70.121, 70.22, 78.17, 47, 70.16, 70.17

[56] References Cited

U.S. PATENT DOCUMENTS

| 4,983,418 | 1/1991 | Murphy et al. .................... 424/47 |
|---|---|---|
| 5,034,218 | 7/1991 | Duvel ............................. 424/70 |
| 5,362,485 | 11/1994 | Hayama et al. . |
| 5,468,477 | 11/1995 | Kumar et al. ................. 424/78.17 |
| 5,618,524 | 4/1997 | Bolich, Jr. et al. . |

FOREIGN PATENT DOCUMENTS

| 370764 | 5/1990 | European Pat. Off. . |
|---|---|---|
| 388582 | 9/1990 | European Pat. Off. . |
| 437075 | 7/1991 | European Pat. Off. . |
| 463 780 | 1/1992 | European Pat. Off. . |
| 582 152 | 2/1994 | European Pat. Off. . |
| 56-129300 | 10/1981 | Japan . |
| 7-508060 | 9/1995 | Japan . |
| 9323009 | 11/1993 | WIPO . |
| 9503776 | 2/1995 | WIPO . |
| 9523581 | 9/1995 | WIPO . |

*Primary Examiner*—Jyothsna Venkat
*Attorney, Agent, or Firm*—Finnegan, Henderson, Farabow, Garrett & Dunner, L.L.P.

[57] ABSTRACT

The present invention relates to a cosmetic or dermatological composition for the treatment of keratinous material, in particular the hair, comprising, in a cosmetically or dermatologically acceptable medium, at least one grafted silicone polymer, containing a polysiloxane skeleton grafted with non-silicone organic monomers and at least one anionic polymer in an anionic polymer/grafted silicone polymer weight ratio of between 0.25 and 15.

The compositions according to the invention are used in particular as rinse-out products or as leave-in products, in particular for the washing, care and conditioning of the hair, for maintaining the hairstyle or for shaping the hairstyle.

31 Claims, No Drawings

COMPOSITION FOR THE TREATMENT OF KERATINOUS MATERIAL, COMPRISING AT LEAST ONE GRAFTED SILICONE POLYMER CONTAINING A POLYSILOXANE SKELETON GRAFTED WITH NON-SILICONE ORGANIC MONOMERS AND AT LEAST ONE ANIONIC POLYMER

This application is a 371 of PCT/FR96/01432 filed Sep. 16, 1996.

The present invention relates to a cosmetic or dermatological composition for the treatment of keratinous material, in particular the hair, comprising at least one grafted silicone polymer, containing a polysiloxane skeleton grafted with non-silicone organic monomers and at least one anionic polymer.

Grafted silicone polymers are known in the state of the art, such as those described in patent applications EP-A-0,582,152 and WO 93/23009. These polymers are proposed in hair compositions for their styling properties. However, when these polymers are used, the hold of the hairstyle and the feel of the hair are not satisfactory.

The Applicant has discovered, surprisingly, that by combining at least one grafted silicone polymer with at least one anionic polymer in an anionic polymer/grafted silicone polymer weight ratio of between 0.25 and 15, properties of hair softness and feel are obtained which are substantially superior to those obtained with each polymer used alone.

The composition according to the invention is thus essentially characterized in that it comprises, in a cosmetically or dermatologically acceptable medium, at least one grafted silicone polymer, containing a polysiloxane skeleton grafted with non-silicone organic monomers and at least one anionic polymer in an anionic polymer/grafted silicone polymer weight ratio of between 0.25 and 15.

In the following text, in accordance with that which is generally accepted, the term silicone polymer is understood to denote any organosilicon polymer or oligomer with a branched or crosslinked, linear or cyclic structure, of variable molecular weight, obtained by polymerization and/or polycondensation of suitably functionalized silanes, and consisting essentially of a repetition of main units in which the silicon atoms are linked together by oxygen atoms (siloxane linkage $\equiv$Si—O—Si$\equiv$), optionally substituted hydrocarbon radicals being linked directly via a carbon atom to the said silicon atoms. The most common hydrocarbon radicals are alkyl radicals, notably $C_{1-C10}$ alkyl radicals and in particular methyl, fluoroalkyl radicals, aryl radicals and in particular phenyl, and alkenyl radicals and in particular vinyl; other types of radicals which may be linked, either directly or via a hydrocarbon radical, to the siloxane chain are, notably, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups and anionic groups such as carboxylates, thioglycolates, sulphosuccinates, thiosulphates, phosphates and sulphates, this list not, of course, being limiting in any way (so-called "organomodified" silicones).

According to the present invention, the silicone polymer or polymers which must be used are those which comprise a main chain of silicone (or polysiloxane ($\equiv$Si—O—)$_n$) on which is grafted, inside the said chain as well as optionally on at least one of its ends, at least one organic group containing no silicone.

These silicone polymers may be existing commercial products or may be obtained according to any means known to those skilled in the art, in particular by reaction between (i) a starting silicone correctly functionalized on one or more of these silicon atoms and (ii) a non-silicone organic compound which is itself correctly functionalized with a function which is capable of reacting with the functional group or groups carried by the said silicone, forming a covalent bond; a standard example of such a reaction is the hydrosilylation reaction between $\equiv$Si—H groups and $CH_2$=CH— vinyl groups, or alternatively the reaction between —SH thiofunctional groups and these same vinyl groups.

Examples of silicone polymers which are suitable for carrying out the present invention, as well as their particular mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thiofunctional groups.

According to the present invention, the said anionic monomers containing ethylenic unsaturation are preferably chosen, alone or as a mixture, from linear or branched, unsaturated carboxylic acids optionally partially or totally neutralized in the form of a salt, it being possible for this or these unsaturated carboxylic acid or acids more particularly to be acrylic acid, methacrylic acid, maleic acid, maleic anhydride, itaconic acid, fumaric acid and crotonic acid. The suitable salts are, in particular, alkali metal, alkaline-earth metal and ammonium salts. Similarly, it will be noted that in the final grafted silicone polymer, the organic group of anionic nature which comprises the result of the radical (homo)polymerization of at least one anionic monomer of unsaturated carboxylic acid type may be, after reaction, post-neutralized with a base (sodium hydroxide, aqueous ammonia etc.) to bring it into the form of a salt.

According to the present invention, the hydrophobic monomers containing ethylenic unsaturation are preferably chosen, alone or as a mixture, from alkanol esters of acrylic acid and/or alkanol esters of methacrylic acid. The alkanols are preferably $C_1$–$C_{18}$ and more particularly $C_1$–$C_{12}$. The preferred monomers are chosen from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl(meth)acrylate and stearyl (meth)acrylate, or mixtures thereof.

One family of grafted silicone polymers which is particularly suitable for carrying out the present invention consists of silicone polymers containing in their structure the unit of formula (I) below:

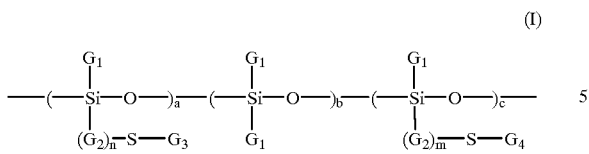

(I)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (I) above has at least one, and more preferably all, of the following characteristics:

the radicals $G_1$ denote an alkyl radical, preferably the methyl radical;

n is non-zero, and the radicals $G_2$ represent a divalent $C_1$–$C_3$ radical, preferably a propylene radical;

$G_3$ represents a polymer radical resulting from the (homo) polymerization of at least one monomer of the carboxylic acid type containing ethylenic unsaturation, preferably acrylic acid and/or methacrylic acid;

$G_4$ represents a polymer radical resulting from the (homo) polymerization of at least one monomer of the ($C_1$–$C_{10}$)alkyl (meth)acrylate type, preferably of the isobutyl or methyl (meth)acrylate type.

Examples of silicone polymers corresponding to formula (I) are, in particular, polydimethylsiloxanes (PDMS) on which are grafted, via a thiopropylene-type linking chain, mixed polymer units of the poly(meth)acrylic acid type and of the polymethyl (meth)acrylate type.

Other examples of silicone polymers corresponding to formula (I) are, in particular, polydimethylsiloxanes (PDMS) on which are grafted, via a thiopropylene-type linking chain, polymer units of the polyisobutyl (meth) acrylate type.

Preferably, the number-average molecular mass of the silicone polymers of the invention ranges approximately from 10,000 to 1,000,000 and even more preferably approximately from 10,000 to 100,000.

The grafted silicone polymer is preferably used in an amount ranging from 0.01 to 15% by weight relative to the total weight of the composition. Even more preferably, this amount ranges from 0.1 to 10% by weight.

According to the invention, any anionic polymer which is known per se may be used. These polymers are preferably fixing polymers, that is to say polymers having the function of temporarily fixing the hairstyle.

Obviously, one or more anionic polymers may be used.

Thus, the anionic polymers generally used are polymers containing groups derived from carboxylic, sulphonic or phosphoric acid and have a molecular weight of approximately between 500 and 5,000,000.

The carboxylic groups are provided by unsaturated mono- or dicarboxylic acid monomers such as those corresponding to the formula:

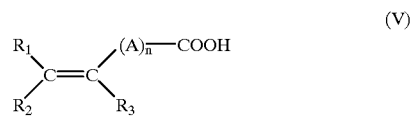

(V)

in which n is an integer from 0 to 10, A denotes a methylene group, optionally connected to the carbon atom of the unsaturated group or to the neighbouring methylene group when n is greater than 1 via a hetero atom such as oxygen or sulphur, $R_1$ denotes a hydrogen atom or a phenyl or benzyl group, $R_2$ denotes a hydrogen atom or a lower alkyl or carboxyl group, and $R_3$ denotes a hydrogen atom or a lower alkyl group, a —$CH_2$—COOH group or a phenyl or benzyl group.

In the abovementioned formula, a lower alkyl radical preferably denotes a group having 1 to 4 carbon atoms and in particular methyl and ethyl.

The anionic polymers containing carboxylic groups which are preferred according to the invention are:

A) homo- or copolymers of acrylic acid or methacrylic acid or salts thereof and in particular the products sold under the name Versicol E or K by the company Allied Colloid, and Ultrahold by the company BASF; copolymers of acrylic acid and of acrylamide sold in the form of their sodium salt under the names Reten 421, 423 or 425 by the company Hercules; sodium salts of polyhydroxycarboxylic acids.

B) copolymers of acrylic or methacrylic acid with a monoethylenic monomer such as ethylene, styrene, vinyl esters, acrylic or methacrylic acid esters optionally grafted on a polyalkylene glycol such as polyethylene glycol and optionally crosslinked. Such polymers are described in particular in French patent 1,222,944 and German application 2,330,956, copolymers of this type containing in their chain an optionally N-alkylated and/or hydroxyalkylated acrylamide unit, as described in particular in Luxembourg patent applications 75370 and 75371 or sold under the name Quadramer by the company American Cyanamid. Mention may also be made of copolymers of acrylic acid and of $C_1$–$C_4$ alkyl methacrylate and the copolymer of methacrylic acid and of ethyl acrylate, sold under the name Luvimer MAEX by the company BASF.

C) copolymers derived from crotonic acid, such as those containing in their chain vinyl acetate or propionate units and optionally other monomers such as allylic or methallylic esters, vinyl ether or vinyl ester of a linear or branched saturated carboxylic acid containing a long hydrocarbon chain, such as those containing at least 5 carbon atoms, it being possible for these polymers optionally to be grafted and crosslinked, or alternatively a vinyl, allylic or methallylic ester of an α- or β-cyclic carboxylic acid. Such polymers are described, inter alia, in French patents 1,222,944, 1,580,545, 2,265,782, 2,265,781, 1,564,110 and 2,439,798. Commercial products falling within this category are the resins 28-29-30, 26-13-14 and 28-13-10 sold by the company National Starch.

D) polymers derived from maleic, fumaric or itaconic acids or anhydrides with vinyl esters, vinyl ethers, vinyl halides, phenylvinyl derivatives, and acrylic acid and esters thereof; these polymers may be esterified. Such polymers are described in particular in U.S. Pat. Nos. 2,047,398, 2,723,248 and 2,102,113 and GB patent 839,805, and in particular those sold under the names Gantrez AN or ES by the company ISP.

Polymers also falling within this category are copolymers of maleic, citraconic or itaconic anhydride and of an allylic or methallylic ester optionally containing an acrylamide or methacrylamide group, an α-olefin, acrylic or methacrylic esters, acrylic or methacrylic acid or vinylpyrrolidone in their chain, the anhydride functions being monoesterified or monoamidated. These polymers are described, for example, in French patents 2,350,384 and 2,35.7,241 by the Applicant.

E) polyacrylamides containing carboxylate groups.

The polymers comprising sulphonic groups are polymers containing vinylsulphonic, styrenesulphonic, napthalenesulphonic or acrylamidoalkylsulphonic units.

These polymers may be chosen in particular from:

salts of polyvinylsulphonic acid having a molecular weight of approximately between 1000 and 100,000, as well as copolymers with an unsaturated comonomer such as acrylic or methacrylic acid and esters thereof, as well as acrylamide or derivatives thereof, vinyl ethers and vinylpyrrolidone.

salts of polystyrenesulphonic acid, the sodium salts having a molecular weight of approximately 500,000 and of approximately 100,000, sold respectively under the names Flexan 500 and Flexan 130 by National Starch. These compounds are described in patent FR 2,198,719.

salts of polyacrylamidesulphonic acids, those mentioned in U.S. Pat. No. 4,128,631 and more particularly polyacrylamidoethylpropanesulphonic acid sold under the name Cosmedia Polymer HSP 1180 by Henkel.

According to the invention, the anionic polymers are preferably chosen from acrylic acid copolymers such as the acrylic acid/ethyl acrylate/N-tert-butylacrylamide terpolymer sold under the name Ultrahold Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acid or anhydride with vinyl esters, vinyl ethers, vinyl halides, phenylvinyl derivatives or acrylic acid and esters thereof, such as the methyl vinyl ether/monesterified maleic anhydride copolymer sold under the name Gantrez ES 425 by the company ISP, copolymers of methacrylic acid and of methyl methacrylate sold under the name Eudragit L by the company Rohm Pharma, the copolymer of methacrylic acid and of ethyl acrylate sold under the name Luvimer MAEX by the company BASF and the vinyl acetate/crotonic acid copolymer sold under the name Luviset CA 66 by the company BASF and the vinyl acetate/crotonic acid/polyethylene glycol terpolymer sold under the name Aristoflex A by the company BASF.

The anionic polymers most particularly preferred are chosen from the methyl vinyl ether/monesterified maleic anhydride copolymer sold under the name Gantrez ES 425 by the company ISP, the copolymers of methacrylic acid and of methyl methacrylate sold under the name Eudragit L by the company Rohm Pharma, the copolymer of methacrylic acid and of ethyl acrylate sold under the name Luvimer MAEX by the company BASF, and the terpolymer of vinylpyrrolidone/acrylic acid/lauryl methacrylate sold under the name Acrylidone LM by the company ISP.

According to the invention, the anionic polymers may also be used in latex or pseudolatex form, that is to say in the form of an aqueous dispersion of insoluble polymer particles.

The anionic polymer/grafted silicone polymer weight ratio is preferably between 0.3 and 8.

According to the invention, the anionic polymer or polymers may represent from 0.1% to 20% by weight, preferably from 0.2% to 15% by weight and even more preferably from 0.5% to 10% by weight, relative to the total weight of the final composition.

The cosmetically or dermatologically acceptable medium preferably consists of water or of a mixture of water and cosmetically acceptable solvents such as monoalcohols, polyalcohols, glycol ethers or fatty acid esters, which may be used alone or as a mixture.

Mention may be made more particularly of lower alcohols such as ethanol and isopropanol, polyalcohols such as diethylene glycol, glycol ethers, and alkyl ethers of glycol or of diethylene glycol.

The grafted silicone polymers according to the invention may be dissolved in the said cosmetically acceptable medium or used in the form of an aqueous dispersion of particles.

The composition of the invention may also contain at least one additive chosen from thickeners, fatty acid esters, fatty acid esters of glycerol, silicones, surfactants, fragrances, preserving agents, sunscreens, proteins, vitamins, polymers, plant, animal, mineral or synthetic oils and any other additive conventionally used in the cosmetics field.

These additives are present in the composition according to the invention in proportions which may range from 0 to 20% by weight relative to the total weight of the composition. The precise amount of each additive depends on its nature and is readily determined by a person skilled in the art.

Obviously, a person skilled in the art will take care to select the optional compound or compounds to be added to the composition according to the invention such that the advantageous properties intrinsically associated with the composition in accordance with the invention are not, or are substantially not, adversely affected by the addition envisaged.

The compositions according to the invention may be in the form of a gel, a milk, a cream, a more or less thickened lotion or a foam.

The compositions according to the invention may be used as rinse-out products or as leave-in products, in particular for the washing, care, conditioning and maintenance of the hairstyle or the shaping of keratinous material such as the hair.

These compositions are more particularly styling products such as hair-setting lotions, blow-drying lotions, fixing compositions (lacquers) and styling compositions. The lotions may be packaged in various forms, in particular in vaporizers, pump-dispenser bottles or in aerosol cans, in order to ensure application of the composition in vaporized form or in the form of a foam. Such packaging forms are indicated, for example, when it is desired to obtain a spray, a lacquer or a foam for fixing or treating the hair.

The compositions may also be shampoos, rinse-out or leave-in compositions to be applied before or after shampooing, dying, bleaching, permanent-waving or straightening of the hair.

When the composition according to the invention is packaged in aerosol form in order to obtain an aerosol foam or lacquer, it comprises at least one propellant which may be chosen from volatile hydrocarbons such as n-butane, propane, isobutane, pentane, a chlorinated and/or fluorinated hydrocarbon, and mixtures thereof. Carbon dioxide, nitrous oxide, dimethyl ether, nitrogen, compressed air and mixtures thereof may also be used as propellants.

The subject of the invention is also a process for the treatment of keratinous material, such as the hair, which consists in applying to the hair a composition as defined above, optionally followed by rinsing with water.

The invention will now be illustrated more fully with the aid of the examples which follow, which should not be considered as limiting it to the embodiments described. (In the following text, AM means active material).

EXAMPLE 1

Styling Spray in a Pump-dispenser Bottle

| | |
|---|---|
| grafted silicone polymer of formula (I) of polymethyl/methylsiloxane structure containing 3-propylthio acid polymethyl methacrylate groups | 5 g |
| acrylic acid/ethyl acrylate/N-tert-butylacrylamide terpolymer (Ultrahold Strong from BASF) | 1 g |
| aminomethylpropanol, 100% neutralization of the two polymers | qs |
| ethanol | qs 100 g |

EXAMPLE 2

Shampoo

| | |
|---|---|
| grafted silicone polymer of formula (I) of structure polymethyl/methylsiloxane containing 3-propylthio polymethacrylic acid groups and 3-propylthio groups | 1 g |
| sodium lauryl ($C_{12}/C_{14}$ 70/30) ether sulphate oxyethylenated with 2.2 mol of ethylene oxide, as an aqueous solution containing 28% AM, sold under the name Empicol ESB 3/FL by the company Albright and Wilson | 10 g AM |
| cocoylbetaine as an aqueous solution containing 28% AM | 4 g AM |
| vinyl acetate/crotonic acid/vinyl neodecanoate terpolymer sold under the name Resin 28-29-30 by National Starch (neutralized with NaOH) | 1 g AM |
| fragrance, sequestering agent, preserving agent | |
| Water | qs 100 g |

The pH is adjusted to 7.5 by addition of sodium hydroxide.

EXAMPLE 3

Styling Spray in a Pump-dispenser Bottle

| | |
|---|---|
| grafted silicone polymer of formula (I) of structure polymethyl/methylsiloxane containing 3-propylthio polymethacrylic acid groups and 3-propylthio polymethyl methacrylate groups | 0.5 g |
| methacrylic acid/ethyl acrylate/tert-butyl acrylate terpolymer (Luvimer 100 P from BASF) | 5 g |
| aminomethylpropanol, 100% neutralization of the two polymers | qs |
| water | qs 100 g |

EXAMPLE 4

Styling Spray in a Pump-dispenser Bottle

| | |
|---|---|
| grafted silicone polymer of formula (I) of structure polymethyl/methylsiloxane containing 3-propylthio polymethacrylic acid groups and 3-propylthio polymethyl methacrylate groups | 2 g |
| methacrylic acid/acrylic acid/ethyl acrylate/methyl methacrylate copolymer as a 25% aqueous dispersion (Amerhold DR 25 from Amerchol) | 7 g AM |
| Water | qs 100 g |

EXAMPLE 5

Aerosol Styling Spray

| | |
|---|---|
| grafted silicone polymer of formula (I) of structure polymethyl/methylsiloxane containing 3-propylthio polymeth acrylic acid groups and 3-propylthio polymethyl methacrylate groups | 5 g |
| vinyl acetate/crotonic acid/vinyl 4-tert-butylbenzoate (65/10/25) copolymer, as described and prepared in patent FR 2,697,160 | 2.5 g |
| aminomethylpropanol, 100% neutralization of the grafted silicone polymer and of the non-silicone copolymer | qs |
| ethanol | qs 100 g |

Pressurization scheme:

| | |
|---|---|
| above composition | 80 g |
| ternary mixture of n-butane, isobutane and propane (23/55/22), sold under the name "Aerogaz 3,2 N" by the company Elf Aquitaine | 5 g |
| 1,1-difluoroethane (Solkane 152 A from Solvay) | 15 g |

EXAMPLE 6

Aerosol Styling Spray

| | |
|---|---|
| grafted silicone polymer of formula (I) of structure polymethyl/methylsiloxane containing 3-propylthio polymethacrylic acid groups and 3-propylthio polymethyl methacrylate groups | 4.6 g |
| vinyl acetate/crotonic acid/vinyl 4-tert-butylbenzoate (65/10/25) copolymer, as described and prepared in patent FR 2,697,160 | 3 g |
| aminomethylpropanol, 100% neutralization of the grafted silicone polymer and of the non-silicone copolymer | qs |
| ethanol | 38.5 g |
| water | qs 100 g |

Pressurization schema:

| | |
|---|---|
| above composition: | 65 g |
| dimethyl ether | 35 g |

EXAMPLE 7

Two compositions A and B according to the invention were prepared and were compared with compositions C and D each containing only one of the two polymers, and compared with composition E which contains the two polymers but in a ratio not included in the invention. The five compositions were packaged in a pump-dispenser bottle. A panel of five experienced testers evaluated the softness of the hair after treatment with these compositions.

The grading ranged from 0 (poor) to 5 (excellent), that is to say ranging from not soft at all to extremely soft.

The results are collated in the following table:

| In g AM | A (Invention) | B (Invention) | C (Comparative) | D (Comparative) | E (Comparative) |
|---|---|---|---|---|---|
| PSV[1] | 0.5 | 1 | 1.5 | — | 1.3 |
| Gantrez ES 425[2] | 1 | 0.5 | — | 1.5 | 0.2 |
| AMP[3] 100% neutralization of the polymer or polymers | qs | qs | qs | qs | qs |
| Water qs | 100 | 100 | 100 | 100 | 100 |
| R | 2 | 0.5 | — | — | 0.15 |
| Softness | 4 | 4.25 | 3.5 | 3.5 | 3.25 |

R = Gantrez ES 425/PSV
[1]PSV: grafted silicone polymer of formula (I) of structure polymethyl/methylsiloxane containing 3-propyl-thio polymethacrylic acid groups and 3-propylthio polymethyl methacrylate groups.
[2]Gantrez ES 425: methyl vinyl ether/monoesterified maleic anhydride copolymer sold by the company ISP
[3]AMP: 2-Amino-2-methylpropanol Hair treated with compositions A and B according to the invention is softer than hair treated with compositions containing only one of the two polymers. When the two polymers are present in a ratio which is not between 0.25 and 15 (composition E), there is no improvement in the softness of the hair when compared with the polymers used alone (compositions C and D).

What is claimed is:

1. A cosmetic or dermatological composition for treating keratinous material, said composition comprising, in a cosmetically or dermatologically acceptable medium, at least one grafted silicone polymer, said at least one grafted silicone polymer containing a polysiloxane skeleton grafted with at least one non-silicone organic monomer, and at least one anionic polymer, said polymers being present in an anionic polymer/grafted silicone polymer weight ratio ranging from 0.25 to 15,
   wherein said at least one anionic polymer is an acrylic acid/ethyl acrylate/N-tert-butylacrylamido terpolymer, a vinyl acetate/vinyl tert-butylbenzoate/crotonic acid terpolymer or a crotonic acid/vinyl acetate/vinyl neododecanoate terpolymer.

2. A composition according to claim 1, wherein said at least one grafted silicone polymer comprises a main chain of polysiloxane on which is grafted, inside said main chain, as well as optionally on at least one of its ends, at least one organic group containing no silicone.

3. A composition according to claim 1, wherein said at least one grafted silicone polymer can be obtained by radical copolymerization of at least one non-silicone anionic organic monomer containing:
   a) ethylenic unsaturation, and/or
   b) a non-silicone hydrophobic organic monomer having ethylenic unsaturation, and
   c) a polysiloxane having in its main chain at least one functional group that will react with said ethylenic unsaturation of said non-silicone monomers.

4. A composition according to claim 3, wherein said at least one non-silicone anionic organic monomer containing ethylenic unsaturation is selected from linear and branched unsaturated carboxylic, acid or mixture of monomers thereof.

5. A composition according to claim 4, wherein said at least one non-silicone anionic organic monomer containing ethylenic unsaturation is selected from at least one acrylic acid, methacrylic acid, maleic acid, maleic anhydride, itaconic acid, fumaric acid, crotonic acid, alkali metal salt of any of the above, alkaline-earth metal salt of any of the above, and ammonium salt of any of the above.

6. A composition according to claim 3, wherein said non-silicone hydrophobic organic monomer containing ethylenic unsaturation is selected from at least one acrylic acid ester of an alkanol and methacrylic acid ester of an alkanol.

7. A composition according to claim 6, wherein said alkanol having from 1 to 18 carbon atoms.

8. A composition according to claim 6, wherein said non-silicone hydrophobic organic monomer containing ethylenic unsaturation is selected, alone or as a mixture of monomers, from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate methyl (meth)acrylate, tert-butyl (meth)acrylate, tridecyl (meth)acrylate and stearyl (meth)acrylate.

9. A composition according to claim 1, wherein said at least one grafted silicone polymer comprises, on the main silicone chain thereof, at least one organic group of anionic nature, said organic group being capable of being obtained by radical (homo)polymerization of at least one anionic monomer of an unsaturated carboxylic acid, wherein said at least one anionic monomer of an unsaturated carboxylic acid is partially or totally neutralized in the form of a salt.

10. A composition according to claim 1, wherein said at least one grafted silicone polymer is a silicone polymer containing in its structure the unit of formula (I):

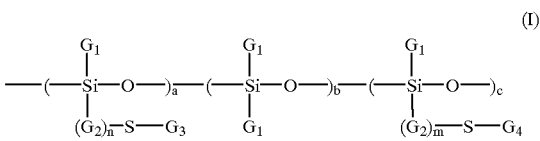

in which the radicals $G_1$, which may each be identical or different, represent hydrogen, a $C_1$–$C_{10}$ alkyl radical, or a phenyl radical; the radicals $G_2$, which may each be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are independently equal to 0 or 1; a is an integer ranging from 0 to 50; b is an integer ranging from 10 to 350; and c is an integer ranging from 0 to 50; with the proviso that one of a or c is other than 0.

11. A composition according to claim 10, wherein said unit of formula (I) has at least one of the following characteristics:

the radicals $G_1$ denote a $C_1$–$C_{10}$ alkyl radical;

n is equal to 1, and each of the radicals $G_2$ represents a divalent $C_1$–$C_3$ radical;

$G_3$ represents a polymer radical resulting from the (homo) polymerization of at least one monomer of a carboxylic acid containing ethylenic unsaturation; or $G_4$ represents a polymeric radical resulting from the (homo)polymerization of at least one monomer of a $C_1$–$C_{10}$ alkyl (meth)acrylate.

12. A composition according to claim 10, wherein said unit of formula (I) simultaneously has each of the following characteristics:

each of the radicals $G_1$ denotes a methyl radical;

n is equal to 1 and the radicals $G_2$ represent a propylene radical;

$G_3$ represents a polymer radical resulting from the (homo) polymerization of at least acrylic acid and/or methacrylic acid; and $G_4$ represents a polymer radical resulting from the (homo) polymerization of at least one monomer of an isobutyl or methyl (meth)acrylate.

13. A composition according to claim 1, wherein the number-average molecular mass of said at least one grafted silicone polymer ranges approximately from 10,000 to 1,000,000.

14. A composition according to claim 13, wherein said number-average molecular mass of said at least one grafted silicone polymer ranges approximately from 10,000 to 100,000.

15. A composition according to claim 1, wherein said at least one grafted silicone polymer is present in an amount ranging from 0.01 to 15% by weight relative to the total weight of the composition.

16. A composition according to claim 15, wherein said at least one grafted silicone polymer is present in an amount ranging from 0.1 to 10% by weight relative to the total weight of the composition.

17. A composition according to claim 1, wherein said anionic polymer/grafted silicone polymer weight ratio ranges from 0.3 to 8.

18. A composition according to claim 1, wherein said at least one anionic polymer is present in an amount ranging from 0.1 to 20% by weight relative to the total weight of the composition.

19. A composition according to claim 18, wherein said at least one anionic polymer is present in an amount ranging from 0.2 to 15% by weight relative to the total weight of the composition.

20. A composition according to claim 19, wherein said at least one anionic polymer is present in an amount ranging from 0.5 to 10% by weight relative to the total weight of the composition.

21. A composition according to claim 1, said composition further comprising at least one additive selected from the group consisting of thickeners, fatty acid esters, fatty acid esters of glycerol, silicones, surfactants, fragrances, preserving agents, sunscreens, proteins, vitamins, polymers, plant, animal, mineral and synthetic oils.

22. A composition according to claim 1, wherein said cosmetically or dermatologically acceptable medium comprises water or a mixture of water and at least one cosmetically acceptable solvent.

23. A composition according to claim 22, wherein said at least one cosmetically acceptable solvent is a monoalcohol, a polyalcohol, a glycol ether, a fatty acid ester, or a mixture thereof.

24. A composition according to claim 1, wherein said at least one grafted silicone polymer is dissolved in said cosmetically or dermatologically acceptable medium or used in the form of an aqueous dispersion of particles.

25. A composition according to claim 1, wherein said keratinous material is human hair.

26. A composition according to claim 1, which is in the form of a gel, a milk, a cream, a thickened lotion or a foam.

27. A composition according to claim 1, wherein said composition is a hairstyling product.

28. A composition according to claim 1, wherein said composition is a shampoo hair product, or a rinse-out or leave-in hair product to be applied before or after shampooing, dyeing, bleaching, permanent-waving, or straightening of the hair.

29. A composition according to claim 1, wherein said composition is packaged in a vaporizer, a pump-dispenser bottle or an aerosol can to obtain a spray, a lacquer or a foam.

30. A non-therapeutic process for treating keratinous material, said process comprising applying to said keratinous material a composition according to claim 1, optionally followed by rinsing with water.

31. A process according to claim 30, wherein said keratinous material is human hair.

\* \* \* \* \*

UNITED STATES PATENT AND TRADEMARK OFFICE
CERTIFICATE OF CORRECTION

PATENT NO.: 6,086,862

DATED: July 11, 2000

INVENTOR(S): Claude Dubief, Christine Dupuis, and Daniéle Cauwet-Martin

It is certified that an error appears in the above-identified patent and that said Letters Patent is hereby corrected as shown below:

In claim 1, column 9, line 61, change "butylacrylamido" to --butylacrylamide--.

Signed and Sealed this

Seventeenth Day of April, 2001

*Attest:*

NICHOLAS P. GODICI

*Attesting Officer*    *Acting Director of the United States Patent and Trademark Office*